(12) United States Patent
Tagawa et al.

(10) Patent No.: US 9,974,499 B2
(45) Date of Patent: May 22, 2018

(54) RADIATION IMAGING SYSTEM

(71) Applicant: CANON KABUSHIKI KAISHA, Tokyo (JP)

(72) Inventors: Motoki Tagawa, Chigasaki (JP); Kensuke Kobayashi, Tokyo (JP); Hidetomo Suwa, Machida (JP); Masataka Suzuki, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days. days.

(21) Appl. No.: 15/718,710

(22) Filed: Sep. 28, 2017

(65) Prior Publication Data

US 2018/0028135 A1    Feb. 1, 2018

Related U.S. Application Data

(63) Continuation of application No. 14/957,031, filed on Dec. 2, 2015, now Pat. No. 9,801,596.

(30) Foreign Application Priority Data

Dec. 4, 2014    (JP) ................................. 2014-246342
Dec. 4, 2014    (JP) ................................. 2014-246343

(51) Int. Cl.
    *A61B 6/00*    (2006.01)

(52) U.S. Cl.
    CPC .......... *A61B 6/4266* (2013.01); *A61B 6/4233* (2013.01); *A61B 6/4283* (2013.01); *A61B 6/5258* (2013.01)

(58) Field of Classification Search
    CPC ........ A61B 6/4405; A61B 6/032; G01T 1/243
    See application file for complete search history.

(56) References Cited

U.S. PATENT DOCUMENTS

9,820,703 B2 *  11/2017  Wojcik ................. A61B 6/4233
2012/0193548 A1    8/2012  Marcovici

FOREIGN PATENT DOCUMENTS

| CN | 102204826 A | 10/2011 |
| CN | 102210591 A | 10/2011 |
| CN | 103370637 A | 10/2013 |
| EP | 1316844 A1 | 6/2003 |
| EP | 1467226 A1 | 10/2004 |

* cited by examiner

*Primary Examiner* — Don Wong
(74) *Attorney, Agent, or Firm* — Canon U.S.A., Inc., IP Division

(57) ABSTRACT

A radiation imaging system includes: multiple radiation imaging apparatuses each including a radiation detecting panel and an enclosure enveloping the radiation detecting panel. The multiple radiation imaging apparatuses are arrayed so that a part of each of the radiation imaging apparatuses spatially overlap as seen from a radiation irradiation side, and a radiation image is acquired based on image signals from each of the multiple radiation imaging apparatuses. The enclosure of at least one radiation imaging apparatus of the multiple radiation imaging apparatuses is formed so that a radiation transmittance of the enclosure which defines the overlapping region is higher than a radiation transmittance of the enclosure which defines a different region.

12 Claims, 14 Drawing Sheets

RADIATION IMAGING SYSTEM

CROSS REFERENCE TO RELATED APPLICATIONS

The present application is a Continuation of U.S. patent application Ser. No. 14/957,031, filed on Dec. 2, 2015, which claims priority from Japanese Patent Application Nos. 2014-246342 and 2014-246343, both filed Dec. 4, 2014, which are hereby incorporated by reference herein in their entirety.

BACKGROUND OF THE INVENTION

Field of the Invention

The present invention relates to a radiation imaging system that is applicable to medical image diagnosis apparatuses, non-destructive inspection apparatuses, analyzers that use radiation, and so forth.

Description of the Related Art

In recent years, there is demand in the field of medicine, for example, for photography with an elongated observation region (hereinafter referred to as "elongated photography") where the spinal cord, lower body, or entire body of a subject is photographed to comprehend imbalance or abnormalities of the body frame. Particularly, a radiation imaging system which can perform elongated photography by a single-time radiation exposure is more preferable in comparison with a radiation imaging system that performs elongated photography by dividing the observation region into multiple sections and performs radiation exposure multiple times, from the perspective of eliminating bodily movement of the subject and reduced exposure.

Japanese Patent Laid-Open No. 2012-040140 discloses a radiation imaging system where elongated photography can be performed by a single exposure with no image dropout at the seams, by performing photography with an array of multiple radiation imaging apparatuses. In Japanese Patent Laid-Open No. 2012-040140, a control board of a first radiation imaging apparatus disposed closer to the radiation irradiation side than a second radiation imaging apparatus and a pixel array of the second radiation imaging apparatus are each positioned so that the control board of the first radiation imaging apparatus does not overlap the pixel array of the second radiation imaging apparatus as viewed from the irradiation direction, and the portion where the radiation imaging apparatuses overlap. Image information is obtained from the pixel array of the first radiation imaging apparatus regarding radiation by which the overlapped portion is irradiated. An elongated image with no image dropout at the seams can be obtained by tiling the images from both radiation imaging apparatuses.

However, Japanese Patent Laid-Open No. 2012-040140 makes no mention of the effects of the enclosure of the radiation imaging apparatuses on the images, and the enclosure of the first radiation imaging apparatus may generate artifacts in images obtained from the second radiation imaging apparatus. One aspect of the present invention provides a technology which is advantageous in suppressing artifacts that may occur in images obtained from the second radiation imaging apparatus due to the enclosure of the first radiation imaging apparatus.

SUMMARY OF THE INVENTION

A radiation imaging system includes multiple radiation imaging apparatuses each including a radiation detecting panel including multiple pixels arrayed in a two-dimensional matrix and configured to convert radiation into image signals, and an enclosure enveloping the radiation detecting panel. The multiple radiation imaging apparatuses are arrayed so that a part of each of the radiation imaging apparatuses spatially overlap as seen from a radiation irradiation side, and a radiation image is acquired based on image signals from each of the multiple radiation imaging apparatuses. The enclosure of at least one radiation imaging apparatus of the multiple radiation imaging apparatuses is formed so that a radiation transmittance of the enclosure which defines the overlapping region is higher than a radiation transmittance of the enclosure which defines a different region from the region in the part.

Further features of the present invention will become apparent from the following description of exemplary embodiments with reference to the attached drawings.

DESCRIPTION OF THE EMBODIMENTS

Embodiments of the present invention will be described in detail below with reference to the attached drawings. It should be noted, however, that details of the dimensions and structures illustrated in the embodiments are not restricted to those given in the text and the drawings. Note that in the present specification, not only X-rays, but also α rays, β rays, γ rays, particle beams, cosmic rays, and so forth, are also included in radiation.

Figure 1:
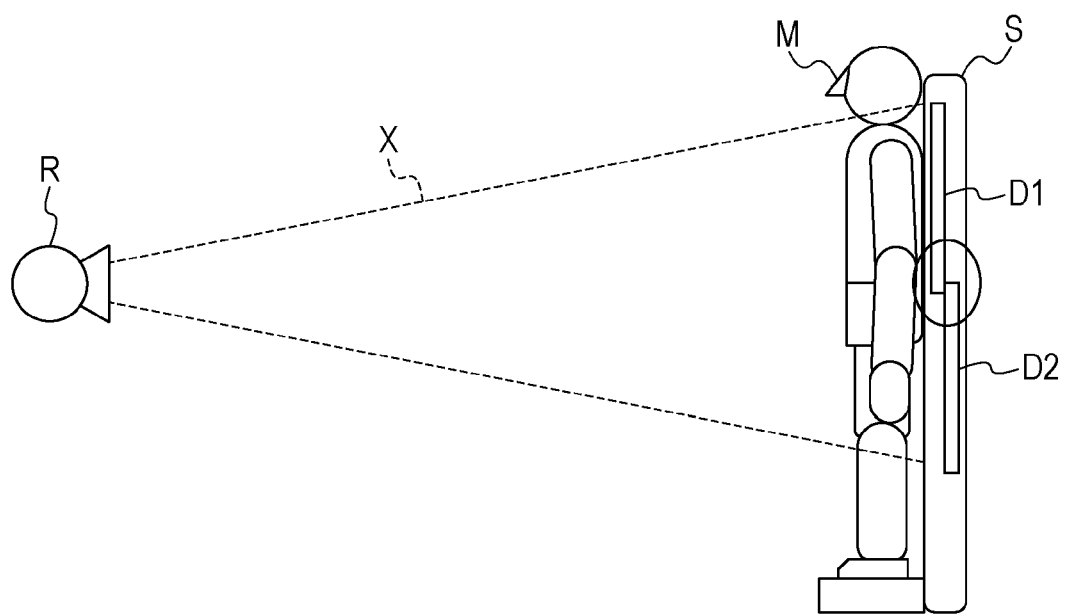
FIG. 1 is a schematic cross-sectional view for describing a radiation imaging system.

A radiation imaging system according to the present invention will first be described with reference to FIG. 1. FIG. 1 is a schematic cross-sectional view for describing the radiation imaging system. A radiation imaging apparatus set S in the radiation imaging system includes a first radiation imaging apparatus D1 and a second radiation imaging apparatus D2. The first radiation imaging apparatus D1 is disposed closer to a radiation generation unit R as compared to the second radiation imaging apparatus D2, i.e., closer to the radiation irradiation side. Part of the first radiation imaging apparatus D1 is disposed so as to be spatially overlapped with a part of the second radiation imaging apparatus D2 as viewed from the radiation irradiation side. Spatially overlapping as used here may be overlapping while in physical contact, or overlapping across space without being in physical contact. A subject M stands on a step placed in front of the radiation imaging apparatus set S, and thus is positioned between the radiation imaging apparatus set S and the radiation generation unit R. Radiation X irradiated from the radiation generation unit R toward the radiation imaging apparatus set S passes through the subject M and reaches the radiation imaging apparatuses D1 and D2, and the radiation captured by the radiation imaging set S is converted into image signals. Image signals acquired by the radiation imaging apparatuses D1 and D2 are subjected to tiling processing at an image processing apparatus omitted from illustration, thereby acquiring a radiation image of the subject M.

First Embodiment

Figure 2A:
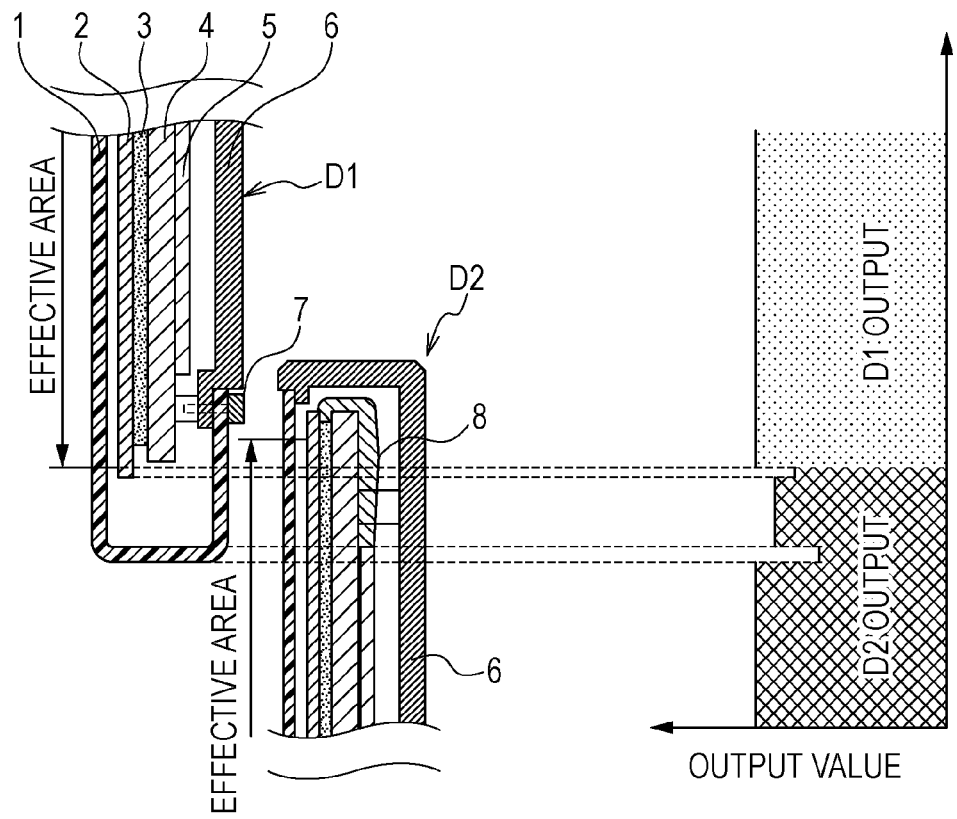
FIGS. 2A and 2B are a cross-sectional schematic and a plan view schematic of a radiation imaging apparatus according to a first embodiment.
Figure 2B:
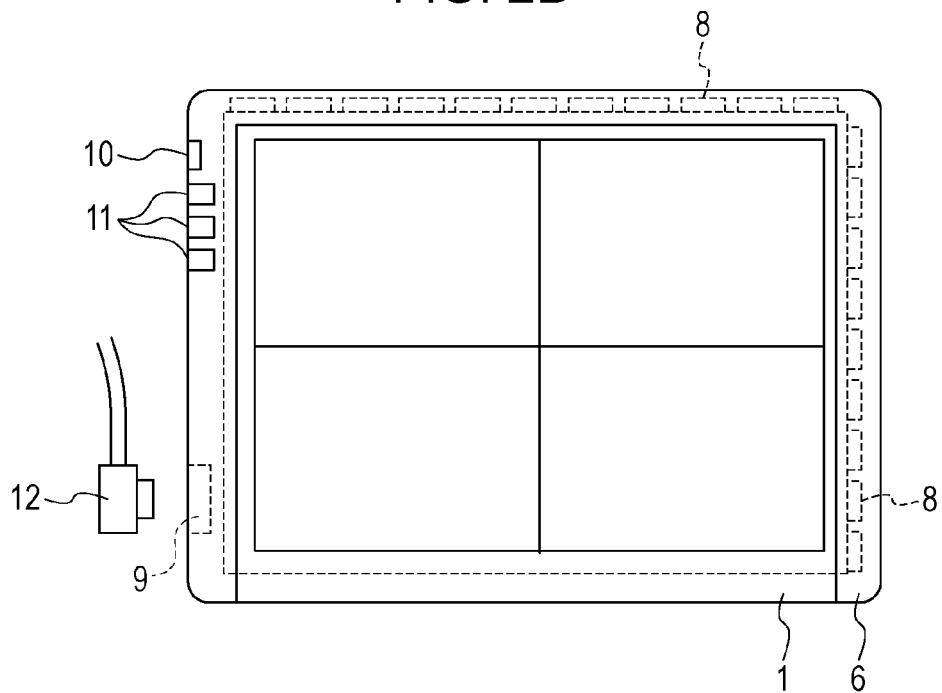

Next, a first embodiment of the present invention will be described with reference to FIGS. 2A and 2B. FIG. 2A is a cross-sectional schematic that is an enlarged view of the encircled portion in FIG. 1 and a conceptual diagram illustrating image signals at that region, and FIG. 2B is a plan view schematic of the first radiation imaging apparatus D1 according to the first embodiment.

The multiple radiation imaging apparatuses D1 and D2 each includes a radiation detecting panel 2, an integrated circuit IC mounted on a flexible circuit board 8 and/or a printed circuit board 5, and first member 1 and second member 6, as illustrated in FIG. 2A. The radiation detecting panel 2 has a pixel array including multiple pixels arrayed in a two-dimensional matrix, and converts irradiated radiation into image signals. The integrated circuit IC mounted on the flexible circuit board 8 and/or printed circuit board 5 is electrically connected to the radiation detecting panel 2. The first member 1 and second member 6 envelop at least the radiation detecting panel 2 and the integrated circuit IC.

The enclosure of at least one radiation imaging apparatus of the multiple radiation imaging apparatuses in the radiation imaging apparatus set S has a part spatially overlapping another radiation imaging apparatus and the radiation transmittance of the part corresponding to the overlapping part is set higher than the radiation transmittance of other parts of the enclosure. More specifically, of the multiple radiation imaging apparatuses of the radiation imaging apparatus set S, the enclosure of the first radiation imaging apparatus D1 disposed on the radiation irradiation side from the second radiation imaging apparatus D2 has the following configuration. The enclosure is formed including the first member 1 and second member 6, such that the radiation transmittance of a first region formed of the first member 1 spatially overlapping the second radiation imaging apparatus D2 as seen from the radiation irradiation side is higher than the radiation transmittance of a second region formed of the second member 6 which faces the integrated circuit IC of the first radiation imaging apparatus D1. According to this configuration, absorption of radiation at the enclosure of the first radiation imaging apparatus D1 spatially overlapping the second radiation imaging apparatus D2 is suppressed. Thus, of the image signals acquired at the second radiation imaging apparatus D2, deterioration of signals acquired from pixels spatially overlapping the first region is suppressed, and artifacts which may occur in the image acquired from the second radiation imaging apparatus D2 due to the enclosure of the first radiation imaging apparatus D1 are suppressed.

A specific example of the radiation imaging apparatuses according to the first embodiment will be described below. The radiation imaging apparatuses D1 and D2 each include, in the enclosure, a junction body obtained by layering the radiation detecting panel 2, a pressure-sensitive adhesive 3, a base 4, and the printed circuit board 5, in that order from the radiation irradiation side. The radiation detecting panel 2 is joined to the base 4 by the pressure-sensitive adhesive 3, and thus the radiation detecting panel 2 is supported by the base 4. The printed circuit board 5 is disposed on the opposite side from the radiation detecting panel 2 across the base 4. The enclosures of the radiation imaging apparatuses D1 and D2 include the first member 1 and second member 6. The first member 1 is made of a material having a high radiation transmittance as compared to the second member 6. The first member 1 making up the first region preferably uses a material having radiation transmittance from the radiation incident direction equivalent to 5 mm alumina or less. CFRP, for example, is used. The region of the first member 1 facing a pixel array of the radiation detecting panel 2 preferably has a radiation transmittance higher than in the first region. On the other hand, the second member 6 making up the second region of the enclosure facing the integrated circuit IC preferably is of a material with higher rigidity than the first member 1 and lower radiation transmittance, metal materials such as aluminum and magnesium being used. The radiation detecting panel 2 includes a pixel array capable of capturing radiation, and peripheral portion on the outer perimeter of the pixel array. The second radiation imaging apparatus D2 is positioned so that the pixel array thereof partially overlaps with the pixel array of the first radiation imaging apparatus D1, thereby yielding a configuration where the pixel array of one or the other of the radiation imaging apparatuses D1 and D2 will acquire image information regardless of the line thereof. The joined radiation image is created by tiling the image signals of the first radiation imaging apparatus D1 and image signals of the second radiation imaging apparatus D2 which have not been acquired by the first radiation imaging apparatus D1. Now, the structures of the first radiation imaging apparatus D1 in an area from the edge of the pixel array of the first radiation imaging apparatus D1 to the edge of the enclosure may be picked up by the second radiation imaging apparatus D2, resulting in artifacts occurring in the joined radiation image. Accordingly, the first region is formed in the present embodiment as a portion where the first member 1 folds around the side wall portion to the rear face portion and is picked up by the second radiation imaging apparatus D2. Accordingly, attenuation of radiation due to absorption of radiation by the enclosure in this region can be suppressed as compared to a case where the second member 6 is used for this portion. By reducing the output deterioration of the radiation images, the image of this region can be subjected to correction processing by combining with information regarding output deterioration amount due to the enclosure in this region, from radiation images acquired beforehand, thereby improving image quality. The first member 1 and the second member 6 are joined using screws 7 outside of the first region, yielding a configuration where the screws 7 are not picked up in the joined radiation images.

The enclosure according to the present embodiment has a generally square shape as illustrated in FIG. 2B. While one side of the four sides is configured using the first member 1, the remaining three sides, and all corner portions, are configured using the second member 6. This configuration ensures strength when dropped on a corner, and overall rigidity of the apparatus. In a case of using CFRP as the first member 1, formability is poor so forming a box shape is difficult. From this point as well, forming just one side of CFRP is advantageous. The enclosure is provided with a power switch 10 for the radiation imaging apparatus, a display unit 11 such as LED or the like to display the power state of the radiation imaging apparatus, and a connection portion 9 connectable to a cable 12 that performs power supply to, and/or transmission/reception of signals with, the integrated circuit IC. These are disposed as regions in the first radiation imaging apparatus D1 other than the first region spatially overlapping the second radiation imaging apparatus D2. The present embodiment yields a configuration where these structures are not picked up in the joined radiation image, by providing the second member 6. The flexible circuit board 8 electrically connected to the printed circuit board 5 is electrically connected to the radiation detecting panel 2 at two mutually orthogonal sides. The flexible circuit board 8 of the first radiation imaging apparatus D1 is disposed at a region other than the first region spatially overlapping the second radiation imaging apparatus D2, thereby yielding a configuration where the flexible circuit board 8 is not picked up in the joined radiation images. Also, the regions of the enclosure excluding the first region are preferably visible from the outside, to prevent installing in the wrong direction.

Second Embodiment

Figure 3A:
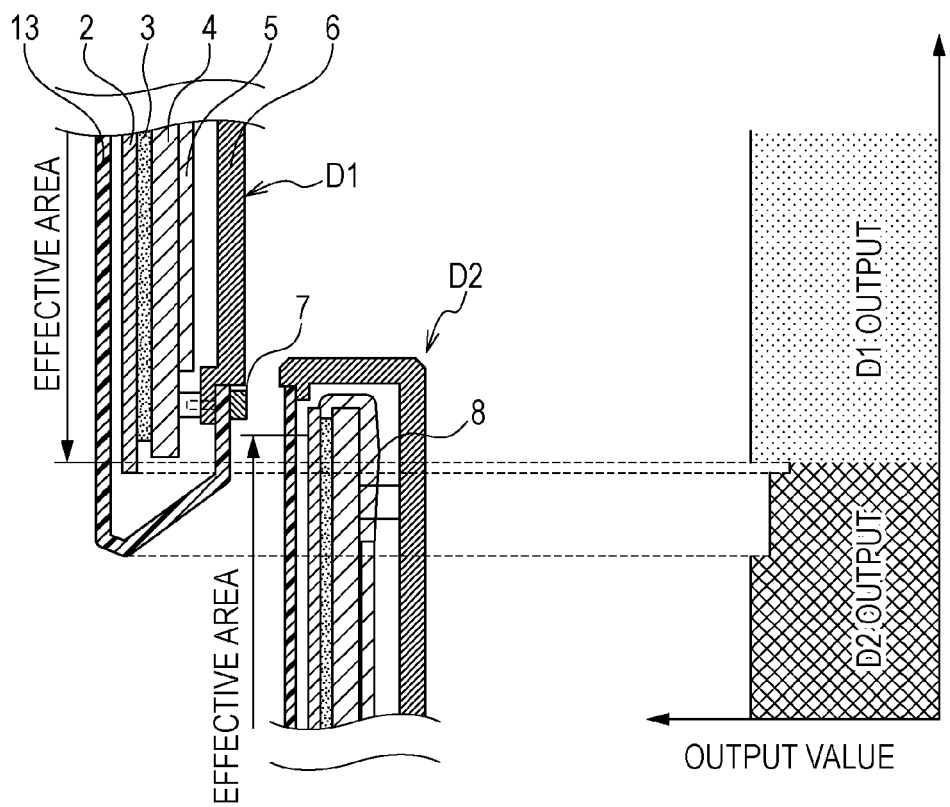
FIGS. 3A and 3B are a cross-sectional schematic and a plan view schematic of a radiation imaging apparatus according to a second embodiment.
Figure 3B:
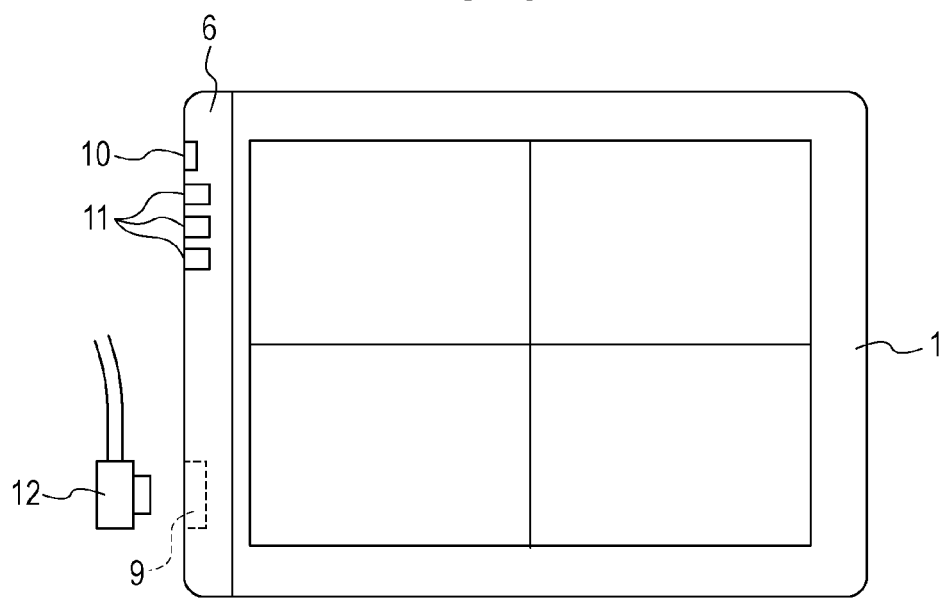

Next, a second embodiment of the present invention will be described with reference to FIGS. 3A and 3B. FIG. 3A is a cross-sectional schematic that is an enlarged view of the encircled portion in FIG. 1 and a conceptual diagram illustrating image signals at that region, and FIG. 3B is a plan view schematic of the first radiation imaging apparatus D1 according to the second embodiment. Configurations the same as those in the first embodiment are denoted with the same reference numerals, and detailed description thereof will be omitted.

The side wall of the enclosure in the first region is configured using the first member 1 in the first embodiment. However, radiation is absorbed at the first member 1 by an amount according to the thickness of the outer shape of the enclosure, so the amount of radiation absorbed is markedly greater as compared to other regions excluding the side wall in the first region, by an amount according to the thickness of the side wall. Accordingly, the second embodiment is configured such that the thickness of the outer shape of the enclosure of the first radiation imaging apparatus D1 in the first region is thinner than the thickness of the outer shape of the enclosure D of the first radiation imaging apparatus in a second region, for example, which is a different region from the first region, as illustrated in FIG. 3A. In particular, a configuration where the thickness of the outer shape of the enclosure of the first radiation imaging apparatus D1 in the first region becomes thinner toward the end of the first region is preferable. According to this configuration, the height of the side wall configured using the first member 1 is lower as compared to the first embodiment, and artifacts in radiation images due to absorption of radiation by the side wall of the enclosure can be suppressed even further.

Further, of the four sides of a general rectangular shape, three sides including the first region are formed using the first member 1, and the remaining one side is formed using the second member 6, as illustrated in FIG. 3B. In this case, the flexible circuit board 8 (omitted from illustration), power switch 10, display unit 11, and connection unit 9, are provided at the one side of the enclosure made of the second member 6. According to this configuration, in a case where the enclosure has a generally rectangular shape as seen from the radiation irradiation side, both a short side and a long side are configured using the first member 1. In a case where a radiation image joined longitudinally is to be obtained, the short sides can be overlapped as the first region, and in a case where a radiation image joined at laterally is to be obtained, the long sides can be overlapped as the first region. Accordingly, freedom of photography is improved with the second embodiment as compared to the first embodiment.

Third Embodiment

Figure 4A:
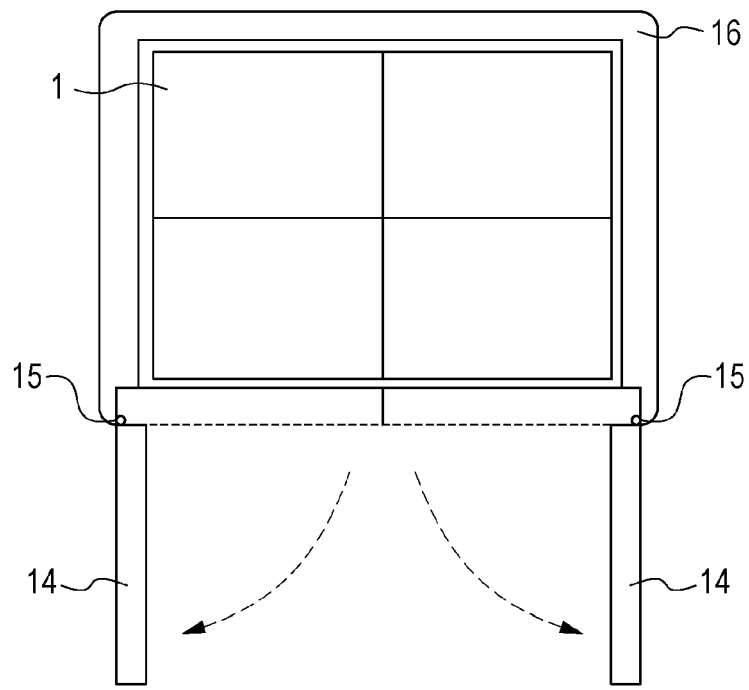
FIGS. 4A and 4B are a cross-sectional schematic and a plan view schematic of a radiation imaging apparatus according to a third embodiment.
Figure 4B:
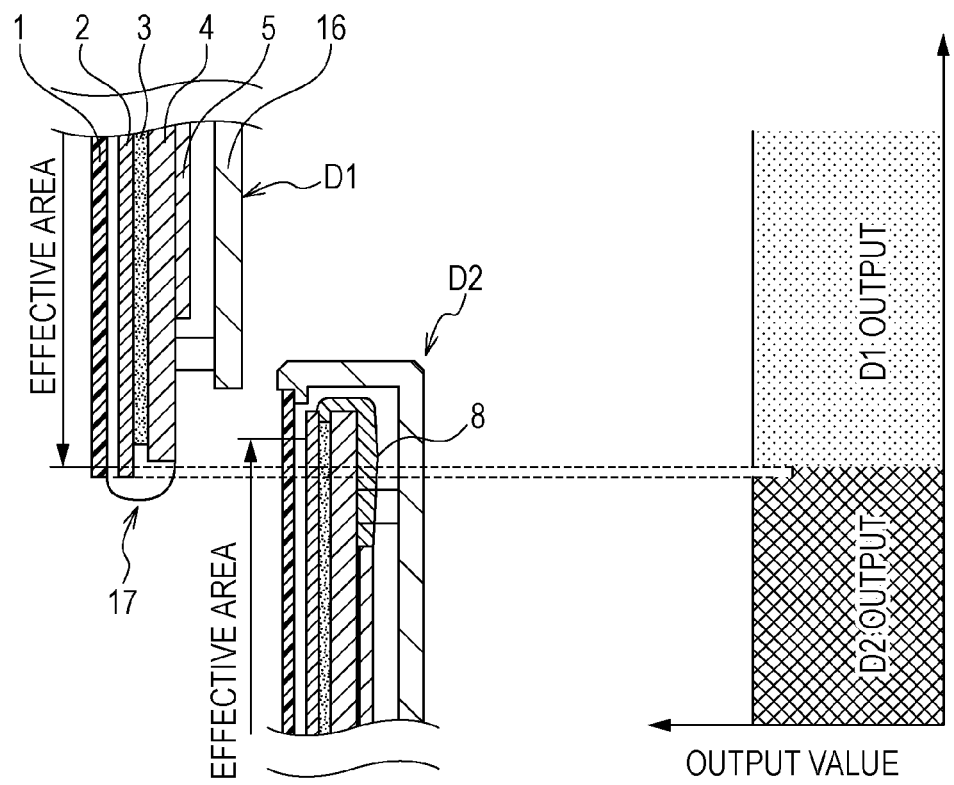
Figure 5:
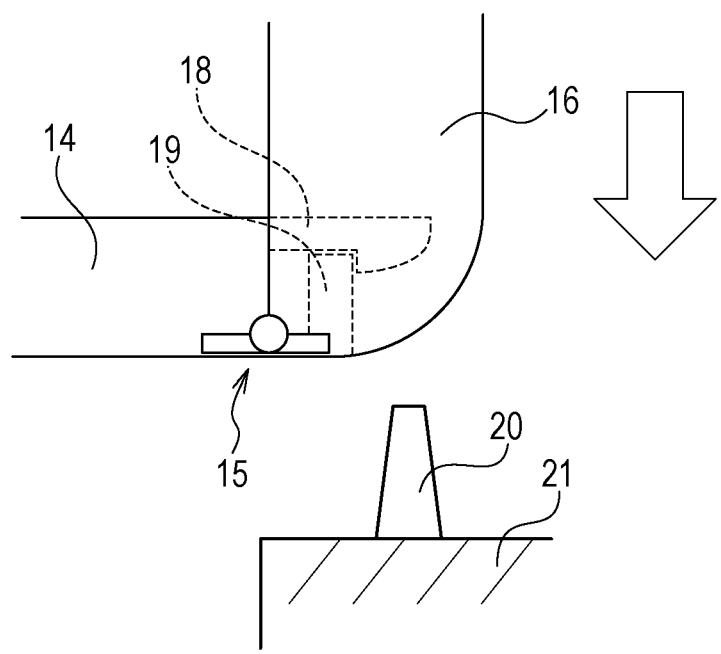
FIG. 5 is an enlarged schematic of the radiation imaging apparatus set according to the third embodiment.

Next, a third embodiment of the present invention will be described with reference to FIGS. 4A, 4B, and 5. FIG. 4A is a plan view schematic of the first radiation imaging apparatus D1 according to the third embodiment, and FIG. 4B is a cross-sectional schematic that is an enlarged view of the encircled portion in FIG. 1 and a conceptual diagram illustrating image signals at that region. FIG. 5 is a conceptual diagram for describing an installation portion for installing a radiation imaging apparatus in a radiation imaging apparatus set S. Configurations the same as those in the first embodiment are denoted with the same reference numerals, and detailed description thereof will be omitted.

The enclosure according to the third embodiment includes a third member 16 that has an opening at one side of the four sides of the generally rectangular shape, a lid 14 capable of closing the opening of the third member 16, and a junction 15 to adjoin the lid 14 to the third member 16 so as to be capable of opening and closing. When a radiation imaging apparatus is used alone, the lid 14 is in a closed state. On the other hand, in a case where elongated photography is performed to acquire a joined radiation image obtained by overlapping parts of radiation imaging apparatuses, the lid 14 is in an open state and one side of the enclosure is opened, and can be moved so that part of the junction body within the enclosure is visible outside of the enclosure. A configuration including a fluorescent member that changes radiation into visible light, and a photoelectric conversion element that converts visible light into electric signals, is used for the pixels of the radiation detecting panel 2 included in the junction body. Accordingly, desired radiation images cannot be obtained if the radiation detecting panel 2 is exposed to external light, so a shielding member 17 is provided to shield the radiation detecting panel 2 in a state where the lid 14 is open. The shielding member 17 essentially makes up a part of the enclosure, the material thereof having a lower radiation absorption rate than the third member 16. In a state where the lid 14 is open, the radiation detecting panel 2 and the shielding member 17 can move to a position spatially overlapping with the second radiation imaging apparatus D2. That is to say, the radiation detecting panel 2 and the shielding member 17 are the first region of the enclosure, thereby suppressing artifacts that can occur in images acquired at the second radiation imaging apparatus D2 due to the enclosure of the first radiation imaging apparatus D1.

An engaging portion 18 is provided on the end of the lid 14 as illustrated in FIG. 5, so as to be fixed in a closed state at a hooking portion 19 provided to the third member 16. On the other hand, a setting portion 21 provided to the radiation imaging apparatus set S is provided with a lock disengaging portion 20. When a radiation imaging apparatus is installed on the setting portion 21 of the radiation imaging apparatus set S, the lock disengaging portion 20 presses the engaging portion 18 upwards. This disengages the fixation of the lid 14, and the lid 14 is in an open state such as illustrated in FIG. 4B. According to this configuration, when installing radiation imaging apparatuses on the radiation imaging apparatus set S to perform elongated photography, the transition to the arrangement for elongated photography is simple.

Fourth Embodiment

Figure 6:
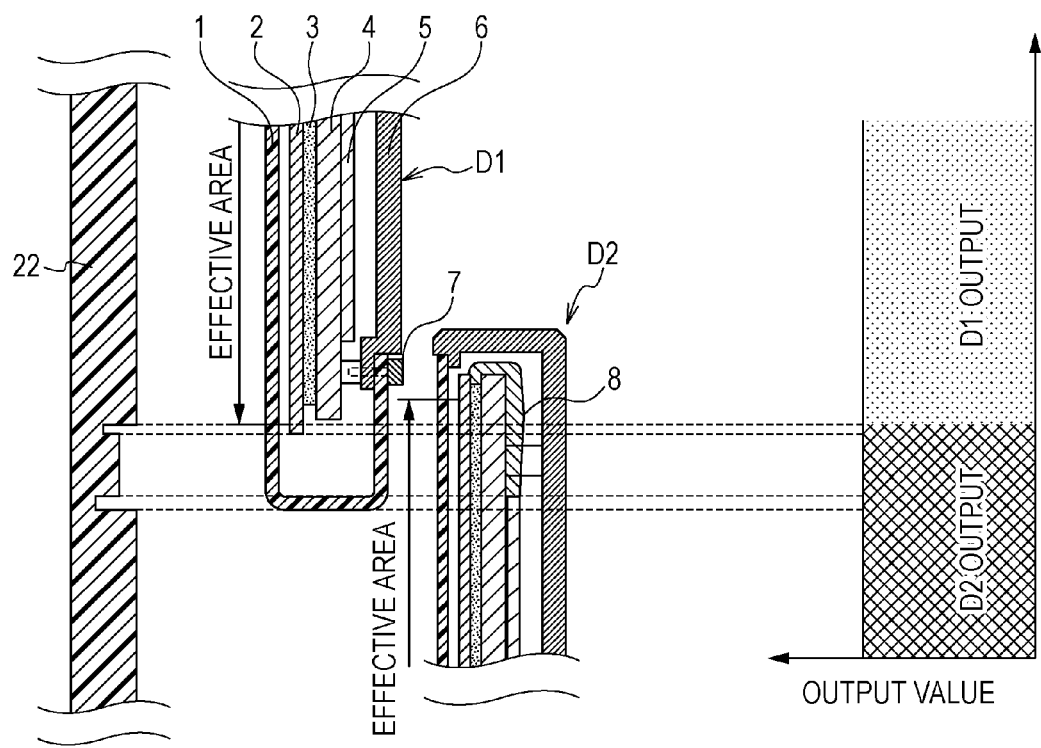
FIG. 6 is a cross-sectional schematic and a plan view schematic of a radiation imaging apparatus according to a fourth embodiment.

Next, a fourth embodiment of the present invention will be described with reference to FIG. 6. FIG. 6 is a cross-sectional schematic that is an enlarged view of the encircled portion in FIG. 1 and a conceptual diagram illustrating image signals at that region. Configurations the same as those in the first embodiment are denoted with the same reference numerals, and detailed description thereof will be omitted.

An accommodation enclosure of the radiation imaging apparatus set S that accommodates multiple radiation imaging apparatuses includes a protective plate 22 to protect the accommodated radiation imaging apparatuses and a scattering ray removing grid (omitted from illustration) from the load of the subject M. Material such as acrylic or polycarbonate can be used for the protective plate 22. The protective plate 22 according to the present embodiment is given distribution in thickness thereof, so as to suppress artifacts in the radiation images. Specifically, the radiation transmittance obtained by adding the three layers of the protective plate 22 at a position corresponding to the first region, the enclosure of the first radiation imaging apparatus D1, and the peripheral portion of the radiation detecting panel 2, is made to be generally equal to the radiation transmittance of the protective plate 22 at portions other than at the first region. This can further suppress artifacts which may occur in images acquired at the second radiation imaging apparatus D2 due to the enclosure of the first radiation imaging apparatus D1.

Fifth Embodiment

Next, a radiation imaging system according to a fifth embodiment of the present invention will be described with reference to FIGS. 7A through 8B. FIGS. 7A through 8B are each schematic cross-sectional views for describing examples of the fifth embodiment.

The radiation imaging apparatus set S in the radiation imaging system in the aforementioned drawings includes the first radiation imaging apparatus D1, the second radiation imaging apparatus D2, and a third radiation imaging apparatus D3. The first radiation imaging apparatus D1 is disposed closer to the radiation generation unit R as compared to the second radiation imaging apparatus D2, i.e., closer to the radiation irradiation side. Part of the first radiation imaging apparatus D1 is disposed so as to be spatially overlapped with a part of the second radiation imaging apparatus D2 as viewed from the radiation irradiation side. Spatially overlapping as used here may be overlapping while physically in contact, or overlapping across space without being in physical contact. In the example illustrated in FIG. 7A, the third radiation imaging apparatus D3 is disposed at the opposite side of the first radiation imaging apparatus D1 from the radiation generation unit R, i.e., on the opposite side from the radiation irradiation side. Part of the first radiation imaging apparatus D1 is disposed so as to be spatially overlapped with a part of the third radiation imaging apparatus D3 as viewed from the radiation irradiation side. On the other hand, in the example illustrated in FIG. 7B, the third radiation imaging apparatus D3 is disposed closer to the radiation generation unit R as compared to the second radiation imaging apparatus D2, i.e., closer to the radiation irradiation side. Part of the third radiation imaging apparatus D3 is disposed so as to be spatially overlapped with a part of the second radiation imaging apparatus D2 as viewed from the radiation irradiation side. The thickness of the overall radiation imaging apparatus set S is suppressed in the configuration illustrated in FIGS. 7A and 7B. In the configuration illustrated in FIG. 7B, the only radiation imaging apparatus regarding which there is another radiation imaging apparatus spatially overlapping at the radiation irradiation side is the second radiation imaging apparatus D2, so the number of radiation imaging apparatuses affected by spatial overlapping can be reduced.

Figure 8A:
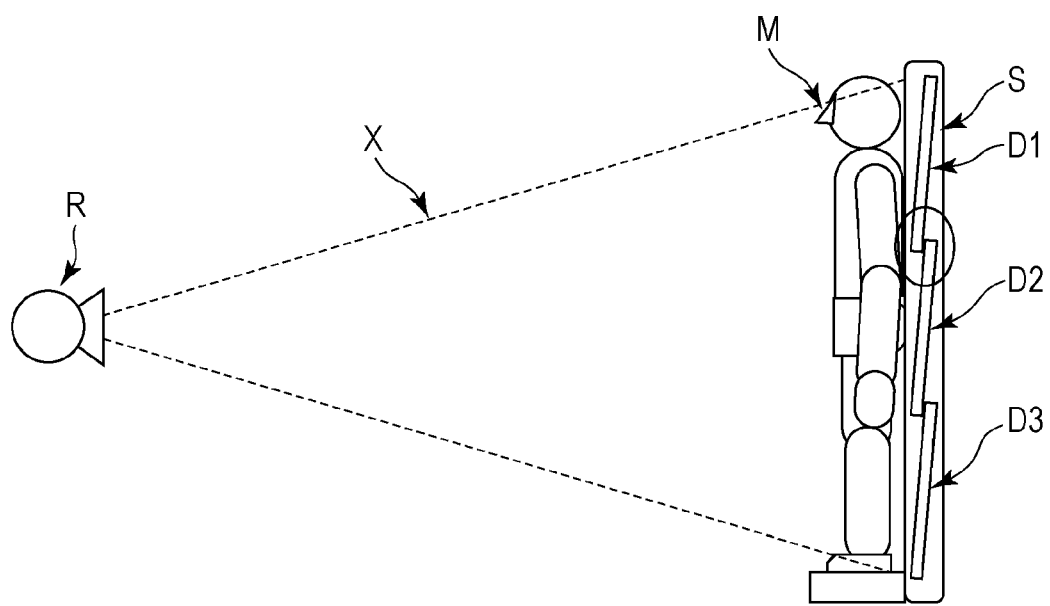
FIGS. 8A and 8B are schematic cross-sectional views for describing the radiation imaging system according to the fifth embodiment.
Figure 8B:
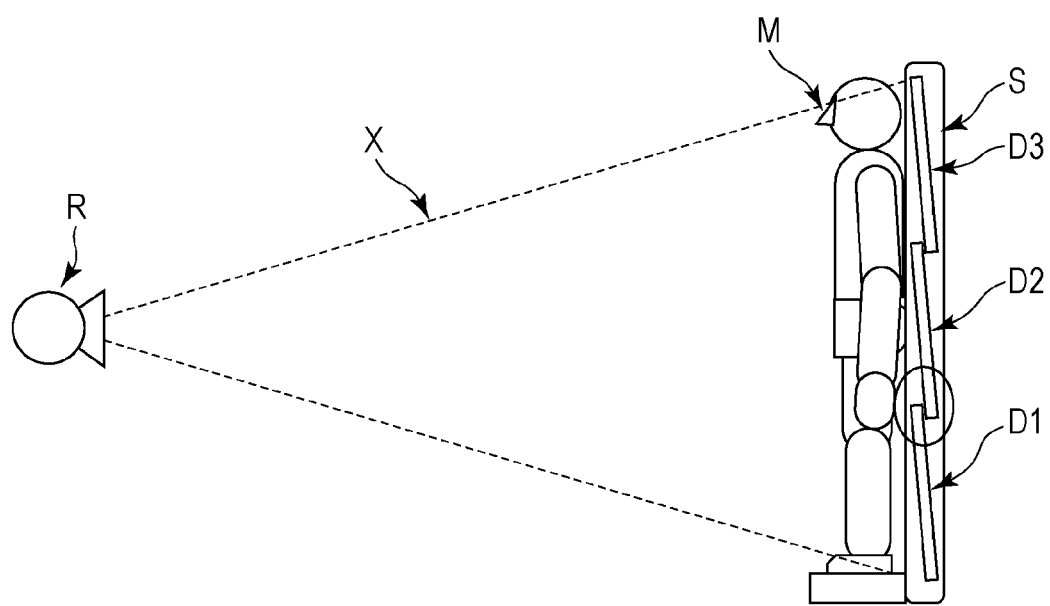

In the configuration illustrated in FIGS. 8A and 8B, the third radiation imaging apparatus D3 is disposed at the opposite side of the second radiation imaging apparatus D2 from the radiation generation unit R, i.e., on the opposite side from the radiation irradiation side. Part of the second radiation imaging apparatus D2 is disposed so as to be spatially overlapped with a part of the third radiation imaging apparatus D3 as viewed from the radiation irradiation side. The subject M stands on a step placed in front of the radiation imaging apparatus set S, and thus is positioned as to the radiation imaging apparatus set S and the radiation generation unit R. Radiation X irradiated from the radiation generation unit R toward the radiation imaging apparatus set pass through the subject M and reach the radiation imaging apparatuses D1 through D3, and are captured by being converted into image signals. Image signals acquired by the radiation imaging apparatuses D1 through D3 are subjected to tiling processing at an image processing apparatus omitted from illustration, thereby acquiring a radiation image of the subject M. While the radiation imaging apparatuses D1 through D3 are disposed tilted as to the enclosure of the radiation imaging apparatus set S in FIGS. 8A and 8B, to suppress thickness of the enclosure of the radiation imaging apparatus set S, the present invention is not restricted to this.

Figure 9A:
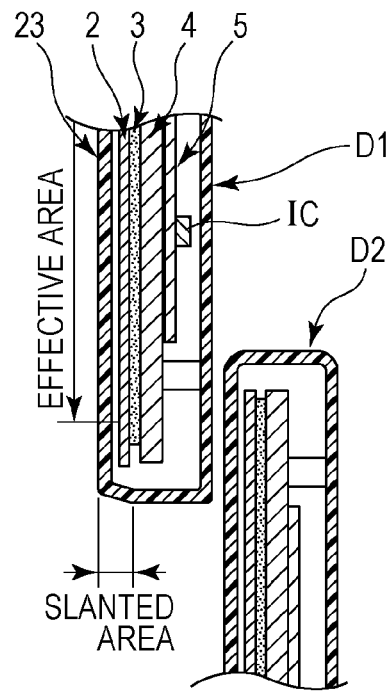
FIGS. 9A and 9B are cross-sectional schematics of a radiation imaging apparatus according to the fifth embodiment.
Figure 9B:
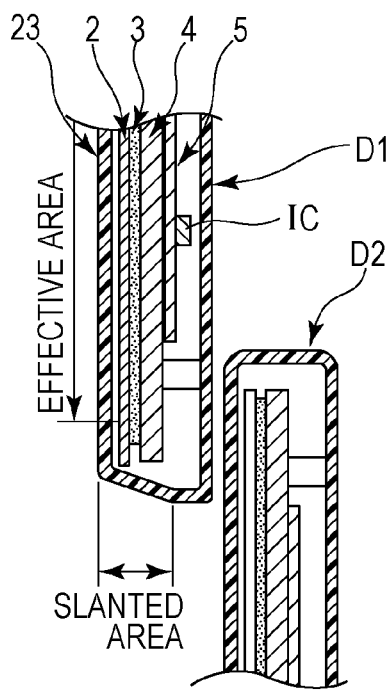

Next, a first embodiment of the present invention will be described with reference to FIGS. 9A and 9B. FIG. 9A is a cross-sectional schematic illustrating an example according to the fifth embodiment, and is an enlarged view of the encircled portion in FIG. 7A. FIG. 9B is a cross-sectional schematic illustrating another example according to the fifth embodiment, and is an enlarged view of the encircled portion in FIG. 7A.

The multiple radiation imaging apparatuses D1 and D2 each includes the radiation detecting panel 2, the integrated circuit IC mounted on the flexible circuit board 8 and/or the printed circuit board 5, and an enclosure 23. The radiation detecting panel 2 has a pixel array including multiple pixels arrayed in a two-dimensional matrix, and converts irradiated radiation into image signals. The integrated circuit IC mounted on the flexible circuit board 8 and/or printed circuit board 5 is electrically connected to the radiation detecting panel 2. The enclosure 23 envelops at least the radiation detecting panel 2 and the integrated circuit IC.

The enclosure 23 of at least one radiation imaging apparatus of the multiple radiation imaging apparatuses in the radiation imaging apparatus set S has the radiation transmittance of a region corresponding to a part thereof spatially overlapping another radiation imaging apparatus set higher than the radiation transmittance of regions other than that region. More specifically, of the multiple radiation imaging apparatuses of the radiation imaging apparatus set S, the enclosure 23 of the first radiation imaging apparatus D1 disposed on the radiation irradiation side from the second radiation imaging apparatus D2 has the following configuration. The enclosure 23 is formed with the thickness of a first region spatially overlapping the second radiation imaging apparatus D2 as viewed from the radiation irradiation side being formed thinner than the maximum thickness of regions other than the first region, such that the radiation transmittance of the first region is higher than the radiation transmittance of a second region facing the integrated circuit IC of the first radiation imaging apparatus D1. More specifically, the thickness of the outer shape of the first region is thinner than the thickness of the outer shape of the second region. According to this configuration, absorption of radiation at the enclosure of the first radiation imaging apparatus D1 spatially overlapping the second radiation imaging apparatus D2 is suppressed. Thus, of the image signals acquired at the second radiation imaging apparatus D2, deterioration of pixels spatially overlapping the first region is suppressed, and artifacts which may occur in the image acquired from the second radiation imaging apparatus D2 due to the enclosure 23 of the first radiation imaging apparatus D1 are suppressed.

A specific example of the radiation imaging apparatuses according to the fifth embodiment will be described below. The radiation imaging apparatuses D1 through D3 each include, in the enclosure 23, a junction body obtained by layering the radiation detecting panel 2, a pressure-sensitive adhesive 3, a base 4, and the printed circuit board 5, in that order from the radiation irradiation side. The radiation detecting panel 2 is joined to the base 4 by the pressure-sensitive adhesive 3, and thus the radiation detecting panel 2 is supported by the base 4. The printed circuit board 5 is disposed on the opposite side from the radiation detecting panel 2 across the base 4.

The enclosure 23 has the thickness of the outer shape of the first region of the first radiation imaging apparatus D1 that spatially overlaps the second radiation imaging apparatus D2 as viewed from the radiation irradiation side so as to be thinner than the thickness of the maximum outer shape of regions other than the first region. More specifically, the thickness of the first region is formed thinner than the thickness of the outer shape of the second region that faces the integrated circuit IC of the first radiation imaging apparatus D1. In particular, the thickness in the first region of the outer shape of the enclosure 23 of the first radiation imaging apparatus D1 is preferably formed to be thinner the closer to the end portion of the first region. In the example illustrated in FIG. 9A, the ridgeline portion connecting the front face of the radiation irradiation side of the enclosure 23 and side face is chamfered at the first region of the first radiation imaging apparatus D1, so as to have a slanted region (slanted area) slanting from a direction parallel to the side face of the enclosure 23. Accordingly, the thickness of the outer shape of the enclosure 23 in the first region is thinner as compared to the thickness of the outer shape of the enclosure 23 in a third region (effective area) facing the second region and pixel array. Also, having the slanted region lowers the height of the side face at the first region of the enclosure 23 as compared with a case where the side face does not have the slanted region, so the radiation transmittance is higher. In a case such as in FIG. 9B where the slanted region is made wider as compared to FIG. 9A, the height of the side face in the first region of the enclosure 23 is even lower, so the radiation transmittance is even higher, and the width of the first region is even wider. The slanted region is not restricted to being formed at the side portion of the sides as viewed from the radiation irradiation side of the enclosure 23 where the first region is included, and may be provided at other side portions where the first region is not included. The radiation detecting panel 2 includes a pixel array capable of capturing radiation, and peripheral portion on the outer perimeter of the pixel array. The second radiation imaging apparatus D2 is positioned so that the pixel array thereof partially overlaps with the pixel array of the first radiation imaging apparatus D1, thereby yielding a configuration where the pixel array of one or the other of the radiation imaging apparatus D1 or D2 will acquire image information regardless of the line thereof. The joined radiation image is created by tiling the image signals of the first radiation imaging apparatus D1 and image signals of the second radiation imaging apparatus D2 which have not been acquired by the first radiation imaging apparatus D1. Now, the structures of the first radiation imaging apparatus D1 in an area from the edge of the pixel array of the first radiation imaging apparatus D1 to the edge of the enclosure 23 may be picked up by the second radiation imaging apparatus D2, resulting in artifacts occurring in the joined radiation image. Thus, the thickness of the outer shape of the first region of the first radiation imaging apparatus D1 that spatially overlaps the second radiation imaging apparatus D2 as viewed from the radiation irradiation side is formed thinner than the greatest thickness of outer shapes other than the first region. Accordingly, attenuation of radiation due to absorption of radiation by the enclosure 23 in this region can be suppressed as compared to a case where the thickness of the outer shape of this position is the same as the thickness at other outer shapes. By reducing the output deterioration of the radiation images, the image of this region can be subjected to correction processing by combining with information regarding output deterioration amount due to the enclosure 23 in this region, from radiation images acquired beforehand, thereby improving image quality.

Figure 10A:
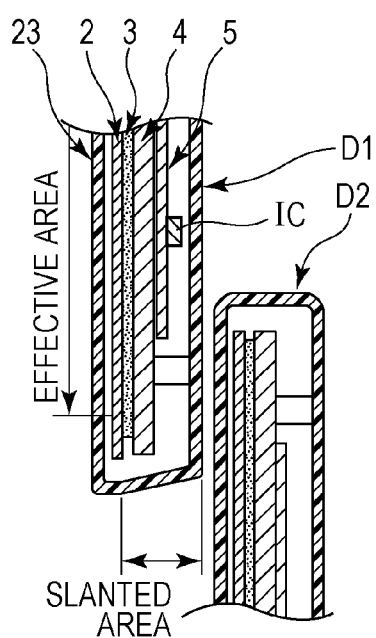
FIGS. 10A through 10C are cross-sectional schematics of the radiation imaging apparatus according to the fifth embodiment.
Figure 10B:
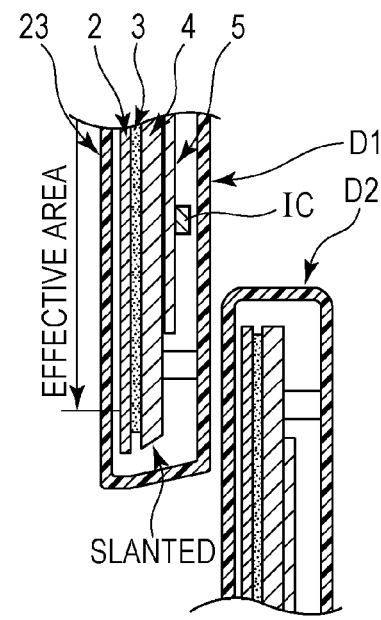
Figure 10C:
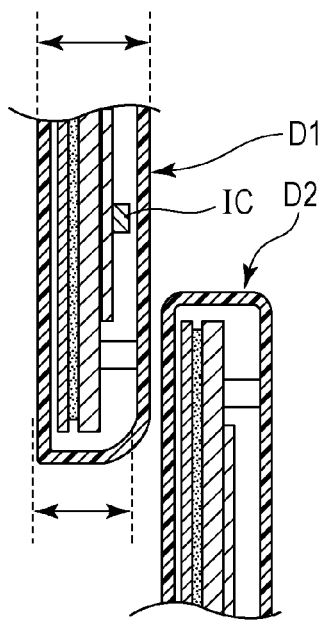

The ridgeline portion connecting the face opposite to the radiation irradiation side of the enclosure 23 and side face may be chamfered at the first region of the first radiation imaging apparatus D1, so as to have a slanted region where the side face of the enclosure 23 slants, as illustrated in FIGS. 10A through 10C. In a case such as in FIG. 10B where the slanted region is made wider as compared to FIG. 10A, the height of the side face in the first region of the enclosure 23 is even lower, so the radiation transmittance is even higher, and the width of the first region is even wider. Also, the slanted region may be a curved face instead of a plane, as illustrated in FIG. 10C and a curved face and plane may be combined. This is applicable to the form where the slanted region is formed at the radiation irradiation side illustrated in FIG. 9A and FIG. 9B, as well.

Figure 11A:
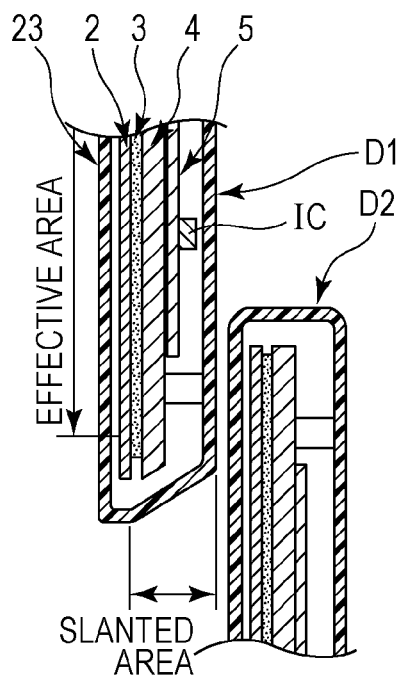
FIGS. 11A through 11C are cross-sectional schematics of the radiation imaging apparatus according to the fifth embodiment.
Figure 11B:
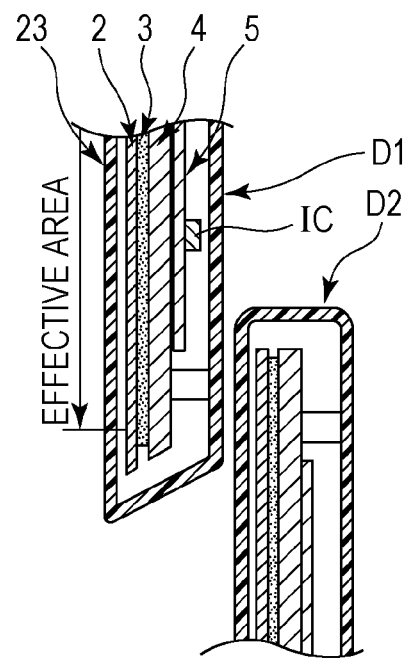
Figure 11C:
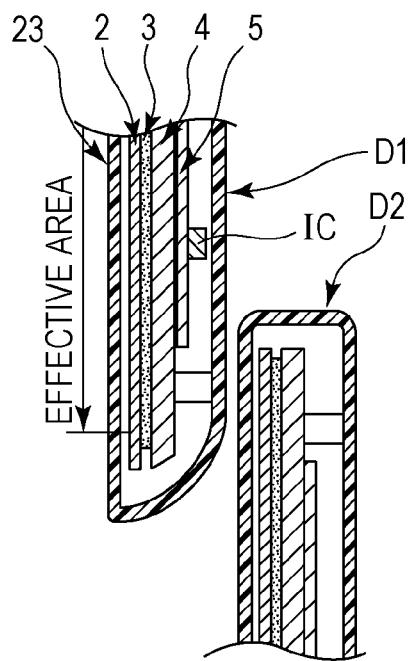

Further, the slanted region in the first region of the first radiation imaging apparatus D1 may extend to a region spatially overlapping part of the base 4 of the first radiation imaging apparatus D1 as viewed from the radiation irradiation side, as illustrated in FIG. 11A through 11C. In such a case, the side face of the base 4 is preferably slanted to match the slanted region, as illustrated in FIG. 11A. Also, the entire side face of the enclosure 23 may be formed into a slanted region at the first region of the first radiation imaging apparatus D1, as illustrated in FIG. 11B. Moreover, the entire side face of the enclosure 23 may be formed into a slanted region having a curved face at the first region of the first radiation imaging apparatus D1, as illustrated in FIG. 11C.

Figure 12:
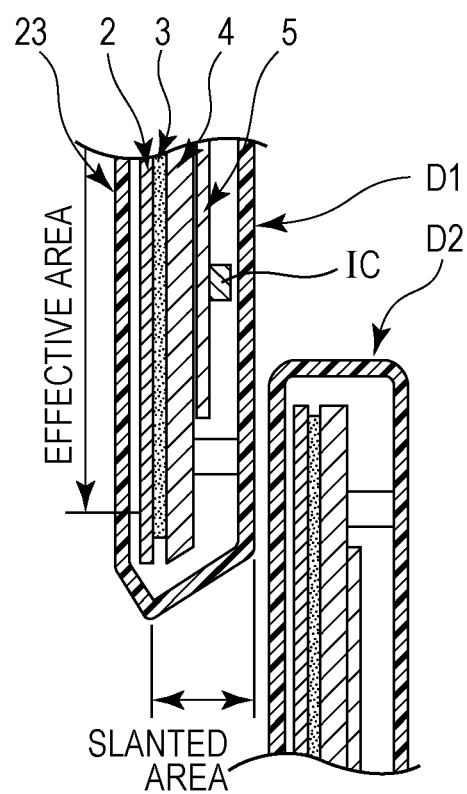
FIG. 12 is a cross-sectional schematic of the radiation imaging apparatus according to the fifth embodiment.

The ridgeline portion connecting the front face of the radiation irradiation side of the enclosure 23 and side face may be chamfered so as to have a slanted region, and the ridgeline portion connecting the face opposite to the radiation irradiation side of the enclosure 23 and the side face may be chamfered so as to have a slanted region, as illustrated in FIG. 12. This sort of configuration is preferably applied to a radiation imaging apparatus used in a radiation imaging apparatus set S such as illustrated in FIGS. 8A and 8B.

Sixth Embodiment

Figure 7A:
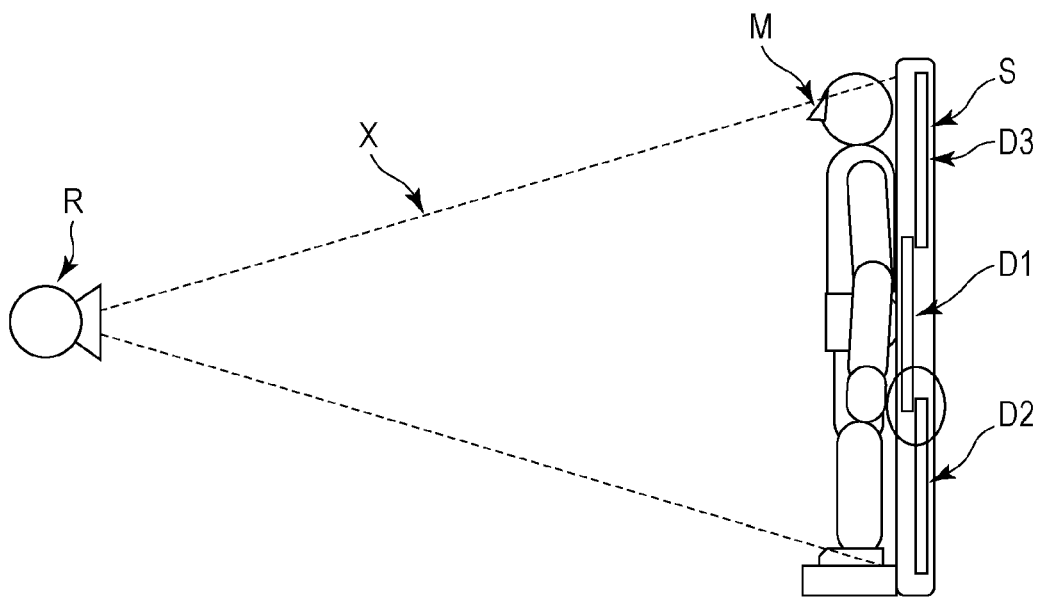
FIGS. 7A and 7B are schematic cross-sectional views for describing a radiation imaging system according to a fifth embodiment.
Figure 7B:
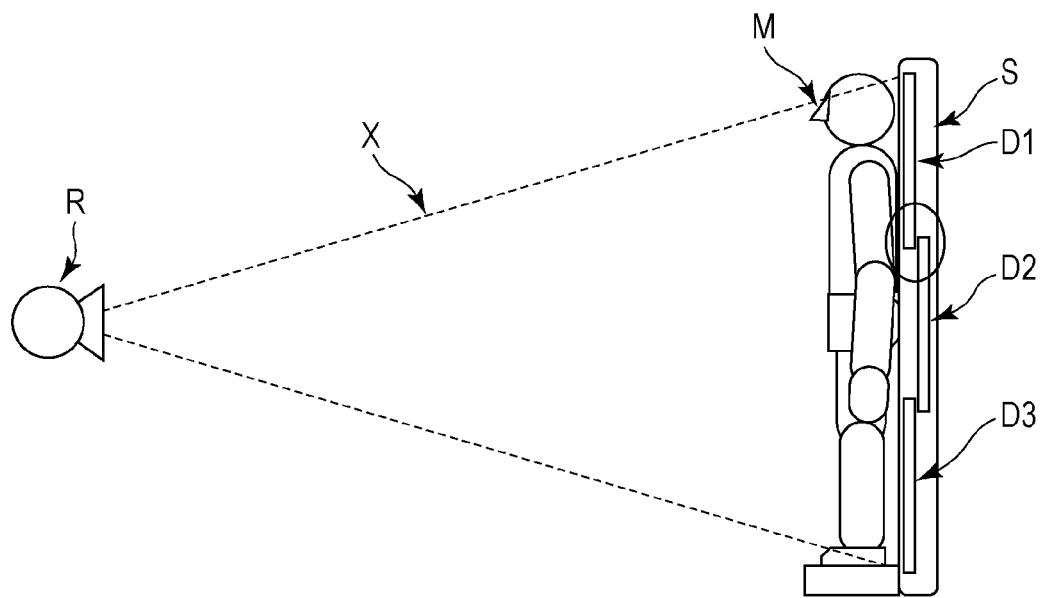
Figure 13A:
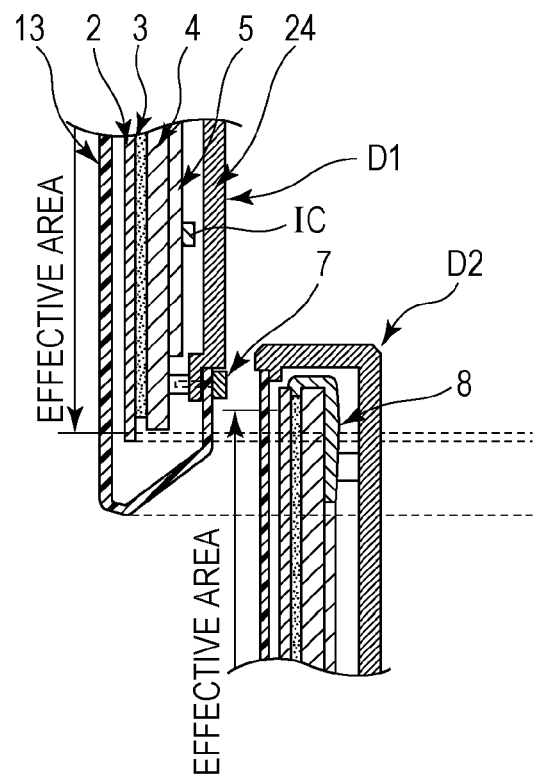
FIGS. 13A and 13B are a cross-sectional schematic and plan view schematic of a radiation imaging apparatus according to a sixth embodiment.
Figure 13B:
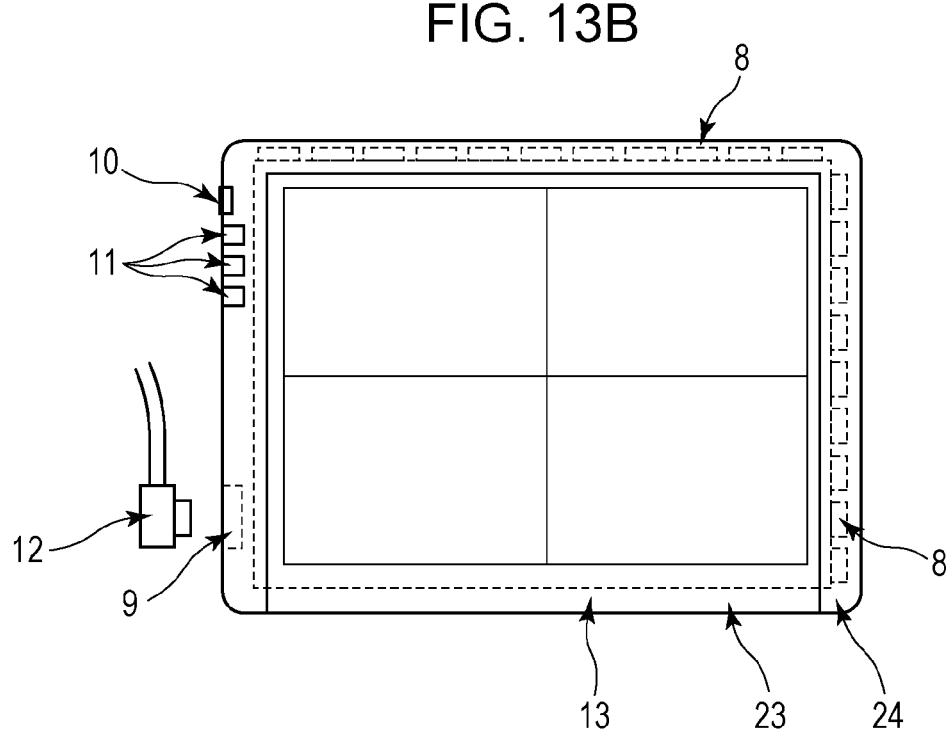

A sixth embodiment will be described with reference to FIGS. 13A and 13B. FIG. 13A is a cross-sectional schematic and is an enlarged view of the encircled portion in FIG. 7A, and FIG. 13B is a plan schematic of a first radiation imaging apparatus D1 according to the sixth embodiment. Configurations the same as those in the fifth embodiment are denoted with the same reference numerals, and detailed description thereof will be omitted.

The sixth embodiment differs from the fifth embodiment with regard to the point that it has the following configuration. The enclosure 23 includes a first member 13 and a second member 24, so that the radiation transmittance in the first region spatially overlapping the second radiation imaging apparatus D2 as viewed from the radiation irradiation side is higher as compared to the radiation transmittance at regions other than that region. According to this configuration, radiation absorption at the enclosure 23 of the first radiation imaging apparatus D1 spatially overlapping the second radiation imaging apparatus D2 is suppressed. Accordingly, deterioration of image signals acquired by the second radiation imaging apparatus D2 from pixels spatially overlapping the first region is suppressed, thereby suppressing artifacts which may occur in images acquired by the second radiation imaging apparatus D2 due to the enclosure 23 of the first radiation imaging apparatus.

The first member 13 is made of a material having a high radiation transmittance as compared to the second member 24. The first member 13 making up the first region preferably uses a material having radiation transmittance from the radiation incident direction equivalent to 5 mm alumina or less. CFRP, for example, is used. The region of the first member 13 facing the pixel array preferably has a radiation transmittance higher than in the first region. On the other hand, the second member 24 making up the second region preferably is of a material with higher rigidity than the first member 13 and lower radiation transmittance. Metal materials such as aluminum and magnesium are used. The first member 13 and the second member 24 are joined using screws 7 outside of the first region, yielding a configuration where the screws 7 are not picked up in the joined radiation images.

The enclosure 23 has a generally square shape as illustrated in FIG. 13B. While one side of the four sides is configured using the first member 13, the remaining three sides, and all corner portions, are configured using the second member 24. This configuration ensures strength when dropped on a corner, and overall rigidity of the apparatus. In a case of using CFRP as the first member 13, formability is poor so forming a box shape is difficult. From this point as well, forming just one side of CFRP is advantageous. The enclosure 23 is provided with the power switch 10 for the radiation imaging apparatus, the display unit 11 such as LED or the like to display the state of the radiation imaging apparatus, and the connection portion 9 connected to the cable 12 that performs power supply to, and/or transmission/reception of signals with, the integrated circuit IC. These are disposed as regions in the first radiation imaging apparatus D1 other than the first region spatially overlapping the second radiation imaging apparatus D2. The present embodiment yields a configuration where these structures are not picked up in the joined radiation image, by providing the second member 24. The flexible circuit board 8 electrically connected to the printed circuit board 5 is electrically connected to the radiation detecting panel 2 at two mutually orthogonal sides. The flexible circuit board 8 of the first radiation imaging apparatus D1 is disposed at a region other than the first region spatially overlapping the second radiation imaging apparatus D2, thereby yielding a configuration where the flexible circuit board 8 is not picked up in the joined radiation images. Also, the regions of the enclosure 23 excluding the first region are preferably visible from the outside, to prevent installing in the wrong direction.

Figure 14:
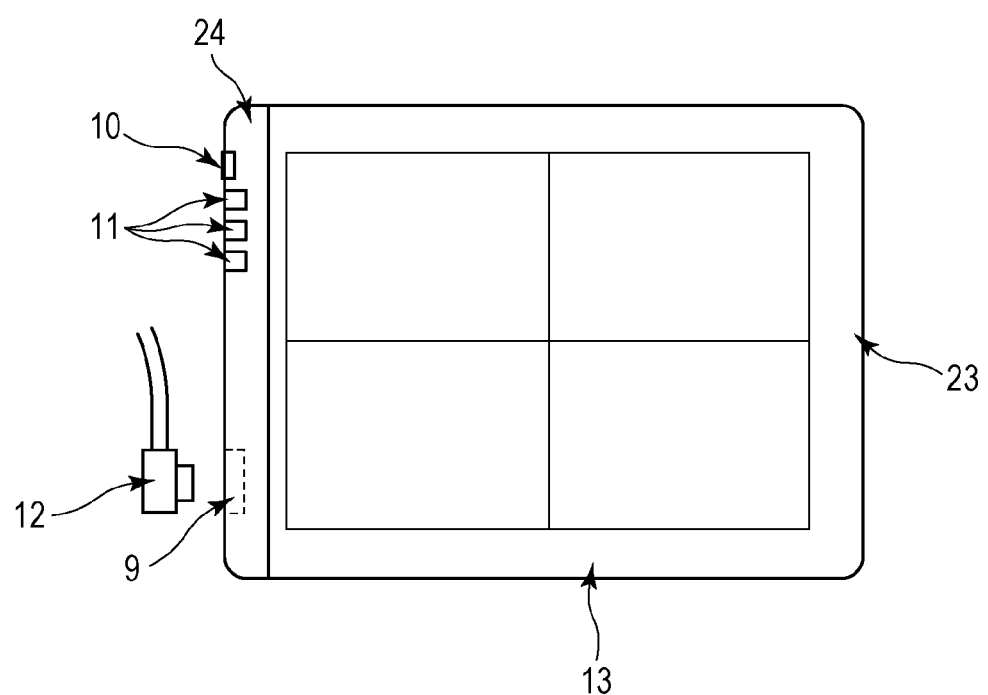
FIG. 14 is a plan view schematic of the radiation imaging apparatus according to the sixth embodiment.

Further, an arrangement may be made such as illustrated in FIG. 14, where, of the four sides of a general rectangular shape, three sides including the first region are formed using the first member 13, and the remaining one side is formed using the second member 24. In this case, the flexible circuit board 8 (omitted from illustration), power switch 10, display unit 11, and connection unit 9, are provided at the one side of the enclosure 23 made of the second member 24. According to this configuration, in a case where the enclosure 23 has a generally rectangular shape as seen from the radiation irradiation side, both a short side and a long side are configured using the first member 13. In a case where a radiation image joined longitudinally is to be obtained, the short sides can be overlapped as the first region, and in a case where a radiation image joined at laterally is to be obtained, the long sides can be overlapped as the first region. Accordingly, freedom of photography is improved with the sixth embodiment as compared to the fifth embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions. Each of the embodiments of the present invention described below can be implemented solely or as a combination of a plurality of the embodiments or features thereof where necessary or where the combination of elements or features from individual embodiments in a single embodiment is beneficial.

What is claimed is:

1. A radiation imaging system, comprising:
a plurality of radiation imaging apparatuses, each radiation imaging apparatus comprising
a radiation detecting panel including a plurality of pixels arrayed in a two-dimensional matrix and configured to convert radiation into image signals, and
an enclosure enveloping the radiation detecting panel;

wherein the plurality of radiation imaging apparatuses are arrayed so that a part of each of the radiation imaging apparatuses spatially overlap as seen from a radiation irradiation side, wherein a power switch for the radiation imaging apparatus and a display unit for displaying a power state of the radiation imaging apparatus are disposed on the enclosure positioned in a region that is different from an overlapping region of the radiation imaging apparatus.

2. The radiation imaging system according to claim 1, wherein, of the plurality of radiation imaging apparatuses, the enclosure of a first radiation imaging apparatus positioned on the radiation irradiation side from a second radiation imaging apparatus is formed.

3. The radiation imaging system according to claim 2, wherein, a thickness of the enclosure of the first radiation imaging apparatus in the overlapping region is smaller than the thickness of the enclosure of the first radiation imaging apparatus in the region that is different from the overlapping region.

4. The radiation imaging system according to claim 2, wherein, a thickness of the enclosure of the first radiation imaging apparatus in the overlapping region becomes smaller toward an outer edge of the enclosure.

5. The radiation imaging system according to claim 2, wherein the radiation transmittance of the overlapping region of the first radiation imaging apparatus is higher than the radiation transmittance of the region that is different from the overlapping region.

6. The radiation imaging system according to claim 2, wherein the enclosure of the first radiation imaging apparatus comprises
a first member arranged to form the overlapping region, and
a second member arranged to form the region that is different from the overlapping region, the second member having a higher rigidity and a lower radiation transmittance than the first member.

7. The radiation imaging system according to claim 6, wherein the enclosure of the first radiation imaging apparatus is configured as a generally rectangular shape, with at least one side of the four sides of the generally rectangular shape formed of the first member and the remaining sides of the four sides formed of the second member.

8. The radiation imaging system according to claim 6, wherein the first member is formed of a material having radiation transmittance equivalent to 5 mm alumina or less.

9. The radiation imaging system according to claim 1, wherein the plurality of radiation imaging apparatuses each further comprises
a flexible circuit board electrically connected to the radiation detecting panel,
a printed circuit board electrically connected to the flexible circuit board, and
a base member configured to support the radiation detecting panel,
and wherein the printed circuit board is disposed to one side of the base member which is an opposite side to a side on which the radiation detecting panel is disposed, and the integrated circuit is mounted on the printed circuit board and/or the flexible circuit board.

10. The radiation imaging system according to claim 1, further comprising:
an accommodation enclosure configured to accommodate the plurality of radiation imaging apparatuses, the accommodation enclosure including a protective plate configured to protect the plurality of radiation imaging apparatuses, the protective plate having a distribution in thickness so that artifacts in the radiation images are suppressed.

11. A radiation imaging system, comprising:
a plurality of radiation imaging apparatuses, each radiation imaging apparatus comprising
a radiation detecting panel including a plurality of pixels arrayed in a two-dimensional matrix and configured to convert radiation into image signals, and
an enclosure enveloping the radiation detecting panel;
wherein the plurality of radiation imaging apparatuses are arrayed so that a part of each of the radiation imaging apparatuses spatially overlap as seen from a radiation irradiation side,
wherein a power switch for the radiation imaging apparatus and a display unit for displaying a power state of the radiation imaging apparatus are disposed on the enclosure positioned in a region that is different from an overlapping region of the radiation imaging apparatus,
wherein, of the plurality of radiation imaging apparatuses, a first radiation imaging apparatus positioned on the radiation irradiation side from a second radiation imaging apparatus is formed,
wherein a thickness of the first radiation imaging apparatus gradually decreases near an edge of the first radiation imaging apparatus.

12. A radiation imaging system, comprising:
a plurality of radiation imaging apparatuses, each radiation imaging apparatus comprising
a radiation detecting panel including a plurality of pixels arrayed in a two-dimensional matrix and configured to convert radiation into image signals, and an enclosure enveloping the radiation detecting panel;
wherein the plurality of radiation imaging apparatuses are arrayed so that a part of each of the radiation imaging apparatuses spatially overlap as seen from a radiation irradiation side,
wherein a power switch for the radiation imaging apparatus and a display unit for displaying a power state of the radiation imaging apparatus are disposed on the enclosure positioned in a region that is different from an overlapping region of the radiation imaging apparatus,
wherein a thickness of an edge of the radiation imaging apparatus in the overlapping region is thinner than a thickness of the radiation imaging apparatus in a region facing a plurality of pixels arrayed in the two-dimensional matrix.

* * * * *